United States Patent
McGaffigan et al.

(10) Patent No.: US 7,025,065 B2
(45) Date of Patent: Apr. 11, 2006

(54) METHOD OF TESTING THERMAL CAUTERY DEVICES

(75) Inventors: Thomas H. McGaffigan, Saratoga, CA (US); Jan M. Echeverry, Saratoga, CA (US); Donielle Boudin, Saratoga, CA (US); Peter Carlotto, Saratoga, CA (US); Huy Le, Saratoga, CA (US)

(73) Assignee: Starion Instruments Corporation, Saratoga, CA (US)

( * ) Notice: Subject to any disclaimer, the term of this patent is extended or adjusted under 35 U.S.C. 154(b) by 293 days.

(21) Appl. No.: 10/713,341

(22) Filed: Nov. 14, 2003

(65) Prior Publication Data

US 2005/0103352 A1    May 19, 2005

(51) Int. Cl.
*A61B 19/00* (2006.01)

(52) U.S. Cl. .......................... 128/898; 606/29; 606/41
(58) Field of Classification Search ............ 606/27–52; 128/898
See application file for complete search history.

(56) References Cited

U.S. PATENT DOCUMENTS

| 5,891,142 | A * | 4/1999 | Eggers et al. | 606/51 |
| 6,626,901 | B1 * | 9/2003 | Treat et al. | 606/29 |
| 6,929,644 | B1 * | 8/2005 | Truckai et al. | 606/51 |

* cited by examiner

*Primary Examiner*—Michael Peffley
*Assistant Examiner*—Pete Vrettakos
(74) *Attorney, Agent, or Firm*—K. David Crockett, Esq.; Crockett & Crockett

(57) ABSTRACT

Thermal cautery and thermal ligating devices improved by the addition of a thermally conductive plate proximate the resistive heating element used in those devices.

6 Claims, 3 Drawing Sheets

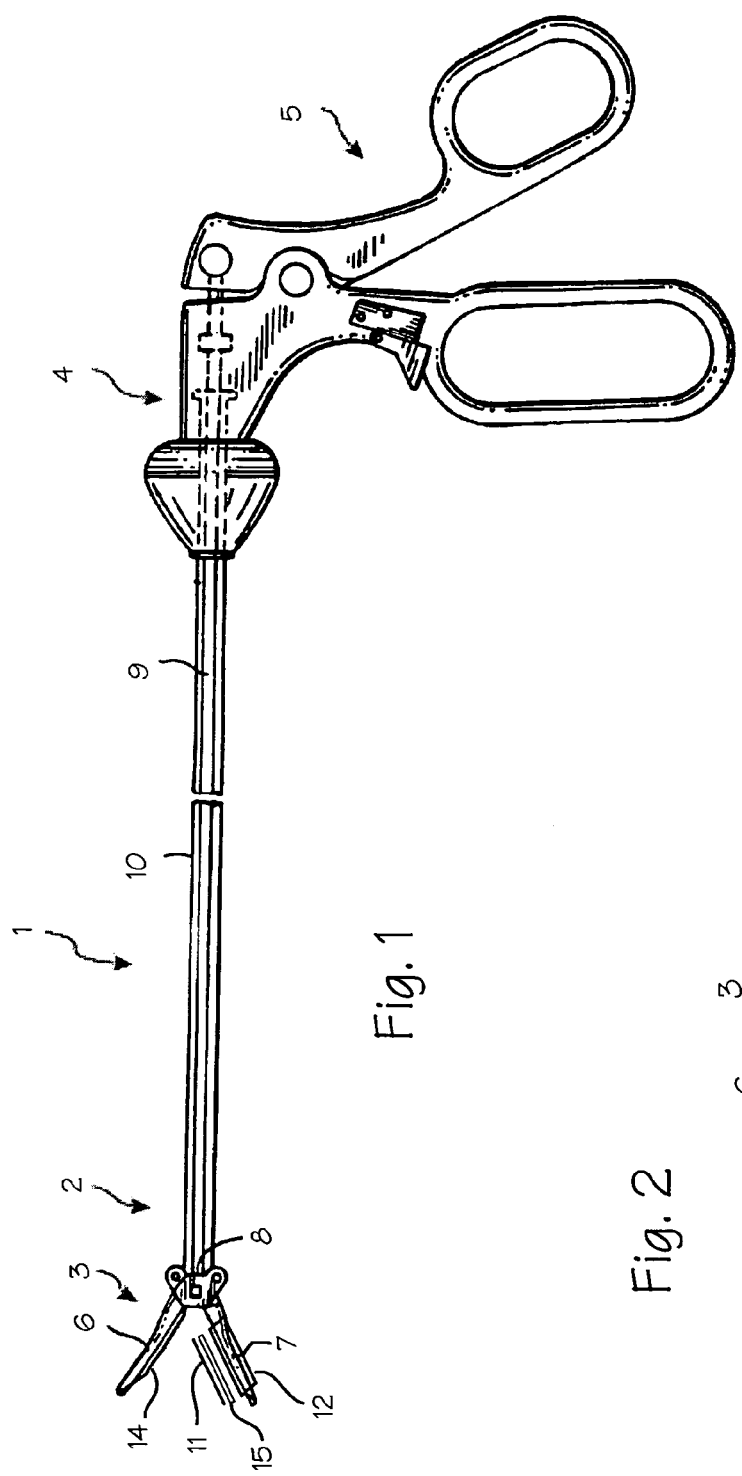
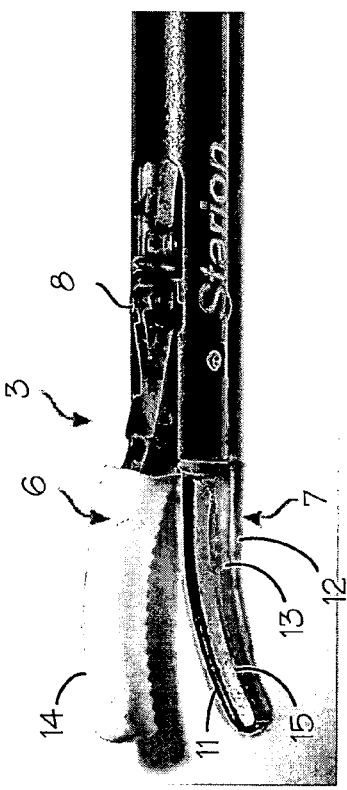
Fig. 1
Fig. 2

METHOD OF TESTING THERMAL CAUTERY DEVICES

FIELD OF THE INVENTIONS

The inventions described below relate to instruments and methods for sealing, joining, and cutting tissue.

BACKGROUND OF THE INVENTIONS

The devices described below provide for improved heat transfer and sealing performance for our Starion® line of thermal cautery forceps and thermal ligating shears, and in instruments such as those disclosed in Treat, et al., *Electrothermal Instrument For Sealing And Joining Or Cutting Tissue*, U.S. Pat. No. 6,626,901 (Sep. 30, 2003) (the disclosure of which is hereby incorporated in its entirety).

SUMMARY

The thermal cautery and thermal ligating devices disclosed in U.S. Pat. No. 6,626,901 are improved by the addition of a thermally conductive plate proximate to the resistive heating element used in those devices.

BRIEF DESCRIPTION OF THE DRAWINGS

FIGS. 1 and 2 illustrate laparoscopic thermal ligating shears designed to provide thermal ligation and division in numerous endoscopic procedures.

DETAILED DESCRIPTION OF THE INVENTIONS

Figure 3:
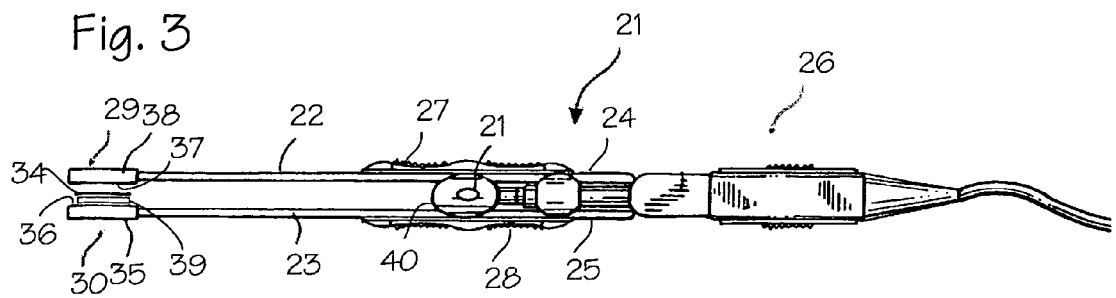
FIG. 3 illustrates a forceps embodiment of a thermal cautery device.

FIGS. 1 and 2 illustrate laparoscopic thermal ligating shears of the type marketed by Starion Instruments, Inc. with the improved heating assembly described below. These shears are designed to provide thermal ligation and division in numerous endoscopic procedures. The shears 1 comprises distal end 2 with remotely operable grasping assembly 3 and a proximal end 4 with a pistol grip actuator 5. The distal end is adapted for insertion into the body of a patient through a laparoscopic access port. The grasping assembly comprises small grasping arms 6 and 7, operably connected to the pistol grip actuator through the pivot section (hinge 8) and actuator rod 9 running through the rigid tube 10, such that operation of the actuator causes the grasping arms to open and close, thereby moving the respective grasping faces into apposition to each other. A resistive heating element (a heater wire or tube) 11 is fixed to the grasping face of the first grasping arm, running over the grasping face from the distal end to the proximal end of the grasping face. The first grasping arm is also covered with a resilient, non-stick, thermally insulative sleeve 12 to provide a resilient pad 13 on the grasping face under the heater wire, between the heater wire and the grasping face. A resilient, thermally insulative sleeve 14 covers the second grasping arm to provide a resilient pad on the grasping face of the second arm. A small thermally conductive but electrically insulative plate or sheet 15 is disposed over the first grasping face, extending laterally across the grasping face and longitudinally under the heating element.

FIG. 2 provides a close up view of the grasping assembly 3, showing the heater wire 11 thermally insulative sleeve 12 on the first grasping arm. Suitable materials for the sleeves and/or resilient pads include polytetrafluoroethylene (PTFE), KAPTON, mica, or silicone. Each sleeve serves to even out pressure applied to tissue and insulates the surfaces of grasping arms electrically and thermally. The thermally conductive but electrically insulative plate is visible between the heating element 11 and the resilient pad 12. As shown in the figure, the plate may be curved and contoured to match the curvature of the grasping face, which in this case is arcuate in the distal-to-proximal aspect, and rounded laterally across the grasping face. This plate serves as a heat spreader to broaden the zone of heat application as illustrated below. The plate may be constructed of a high thermal conductivity metal such as aluminum, copper (and metals of lesser thermal conductivity such as titanium) and the like, a high thermal conductivity ceramics such as boron nitride or aluminum nitride or the like, or a plastic material incorporating a high thermal conductivity metal or ceramic. If the heat spreader is constructed of a material that is an electrical conductor, the heat spreader must be electrically isolated from the resistive heating element. Thus, if comprised of metal, the plate and resistive heating element must be electrically insulated with a high temperature electrical insulator. This may be accomplished with an electrically insulative layer formed of an oxidized surface on the metal plate, such as can be done with metals such as titanium or aluminum. These materials may be covered by a thick layer of oxide of the metal, or by anodizing the metal plate, or with an electrically non-conductive coating on the metal plate or under the resistive wire.

FIG. 3 illustrates thermal cautery forceps of the type marketed by Starion Instruments, Inc. with the addition of the improved heating assembly. The forceps 21 comprises grasping arms in the form of elongate forceps arms 22 and 23 with proximal ends 24 and 25 resiliently mounted to a pivot section (handle section 26). The outer surfaces of forceps arms 22 and 23 are fitted with finger grips 27 and 28 to assist the operator in holding and activating the forceps. The opposing surfaces of the distal tips 29 and 30 of the forceps establish grasping faces which are aligned on each grasping arm so as to meet the grasping face of the other grasping arm upon closure of the grasping arms. Closure of the grasping arms is accomplished manually. The forceps arms may be formed of a suitable resilient material such as stainless steel, plastic, composites, etc. that have the desired combination of stiffness and resilience.

The distal tips include the various elements of the heating assembly. A resistive heating element (a heater wire) 34 is disposed on the grasping face of distal tip 30, secured to the distal end of the grasping arm 23 and extending proximally over the grasping face of the grasping arm toward the proximal end of the grasping arm. The distal tip 30 is also covered with a resilient, non-stick, thermally insulative sleeve 35 to provide a resilient pad 36 on the grasping face under the heater wire, between the heater wire and the grasping face. The grasping face of the opposing distal tip 29 may also be covered by a resilient, non-stick, thermally insulative surface 37, provided as a portion of sleeve 38 disposed over the distal tip 29, in order to provide an anvil surface upon which the heating element acts during operation. The thermally conductive but electrically insulative plate 39 is disposed between the heating element 34 and the resilient pad 36.

Additional elements of the forceps are also shown in FIG. 3. The a finger-operated switch 40 preferably comprises a multi-directional post-in-tube design with a control button 41 and a contact switch disposed in opposition to one of the grasping arms which is operably connected with the power supply (not shown) and the heating element such power cannot be supplied to the heating element unless the contact switch is engaged when a user squeezes the grasping arms.

Figure 4:
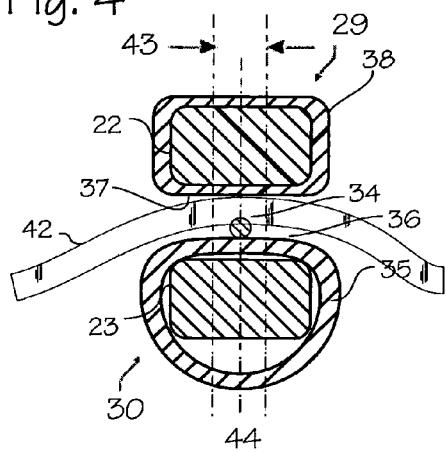
FIG. 4 illustrates the prior art construction of the distal tip of a thermal cautery device.
Figure 5:
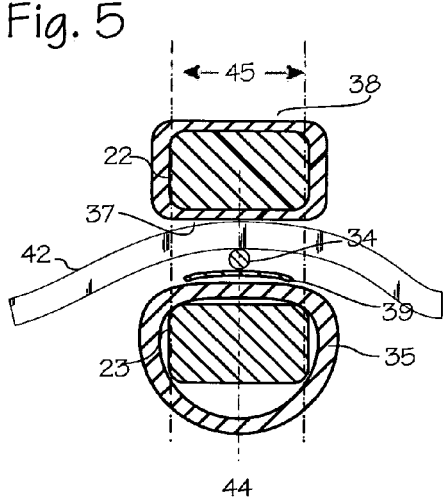
FIGS. 5 and 6 are cross sections of thermal cautery or thermal ligating devices with a thermally conductive plate interposed between the resistive heating element and the grasping face of the distal tip of the grasping arm of the device.

FIG. 4 is a cross section illustrating a prior art construction of the distal tip of a thermal cautery device, while FIG. 5 is a cross section of a thermal cautery device with a thermally conductive plate interposed between the resistive heating element and the grasping face of the distal tip of the grasping arm of the device. The components of the heating assembly components shown in FIG. 3 appear in both figures, with the exception of the plate 39. As discussed in reference to FIG. 3, the grasping face of the distal tip 30 is covered with the resilient pad 36 (which, as illustrated, is a portion of resilient sleeve 35 (the resilient sleeve may also establish a fluid-filled (air or liquid) gap over the outer surface of the distal tip, which helps prevent thermal damage to body tissue in the vicinity of the tissue to be cauterized and ligated)), and the resistive heating element 34 is disposed over the grasping face, over the resilient pad, so that it is located between the grasping faces. The distal tip 29 is covered by the resilient sleeve 38 to establish the resilient pad 37 on the grasping face of this distal tip.

In addition to the structure shown in FIG. 4, FIG. 5 shows the placement of the plate 39, interposed between the heating element and the grasping face of the forceps arm 23. The plate is arcuate, such that it bulges away from the grasping face of forceps arm 23 along its long distal-to-proximal centerline and bows away from the opposing grasping face toward the lateral sides of the device. A typical length of body tissue 42 is shown, held between the grasping faces. In FIG. 4, the extent of heat affected zone in the body tissue is indicated by arrow 43. The high heat generated by the heating wire, combined with light pressure exerted on the body tissue, results in division at line 44. In comparison, as shown in FIG. 5, the extent of heat affected zone in the body tissue, when the plate 39 is used, is indicated by arrow 45. The wide lateral extent of heat affected zone results in a more secure seal of the tissue.

Figure 6:
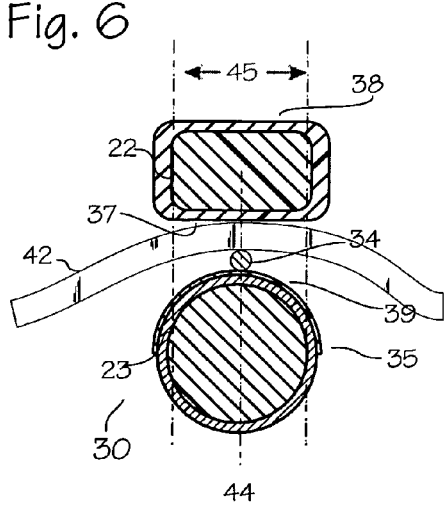
Figure 7:
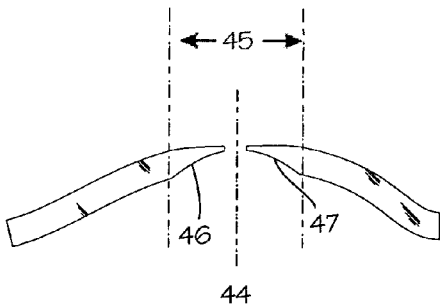
FIG. 7 illustrates the effect of the thermal cautery or thermal ligating devices on a segment of body tissue.

In FIG. 6, which shows the grasping face of the distal tip 30 of the active grasping arm 23, covered by the resilient pad 36, the resistive heating element 34 disposed over the grasping face and the distal tip 29 of the opposing grasping arm with its resilient sleeve 38, along with the plate 39 interposed between the heating element and the grasping face of the active grasping arm 23. In this figure, the distal tip 30 of the active grasping arm 23 is cylindrical, with a substantially circular radial cross section. The resilient sleeve 35 surrounds and closely conforms to the cylindrical grasping arm, and the thermally conductive plate 39 is semi-cylindrical, and is disposed over the sleeve, between the sleeve and the resistive heating element. This embodiment provides for improved contact between the heat spreader and thicker tissues. The resultant divided tissue is shown in FIG. 7, which shows the small area of division on either side of line 44, and the wide lateral extent of thermally sealed tissue boundaries 46 and 47.

Figure 8:
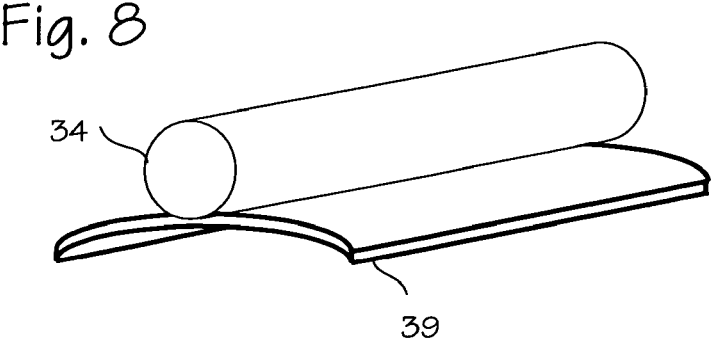
FIGS. 8 and 9 illustrate embodiments of the heating element and thermally conductive plate.
Figure 9:
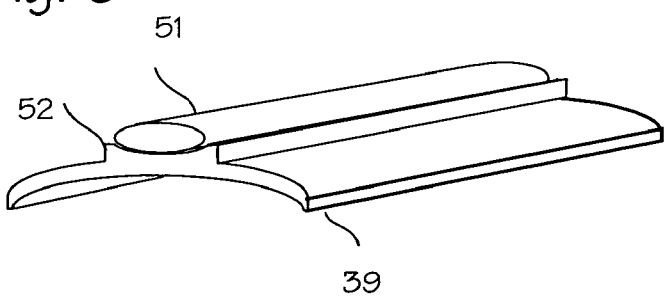
Figure 10:
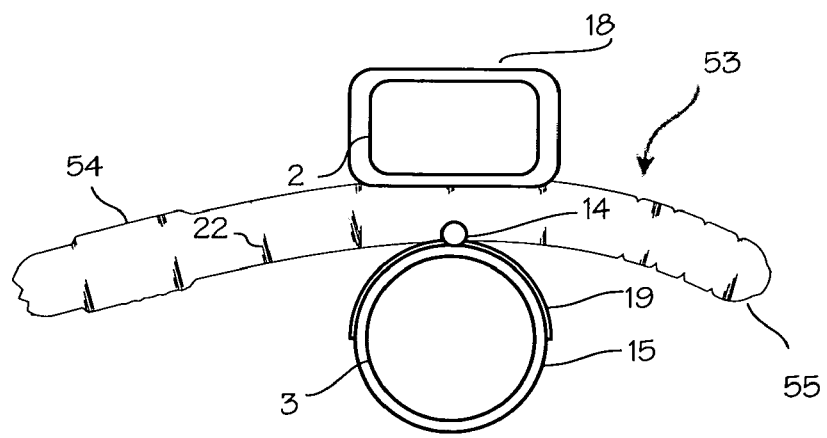
FIG. 10 illustrates a method of testing the thermal cautery or thermal ligating devices.

FIGS. 8 and 9 illustrate the heating element and thermally conductive plate in additional detail. FIG. 8 illustrates the laterally arcuate shape of the plate 39, with a round wire heating element 34 overlying the plate. FIG. 9 illustrates an oval cross-section wire heating element 51 physically and thermally intimate with or joined to the plate with channel beam 52. The channel beam and plate of FIG. 9 may be integrally formed, or formed of discrete components.

The plate greatly increases the amount of heat energy that can be delivered to the tissue prior to cutting the tissue. This increases the seal size (the amount of tissue that is sealed) and the integrity of the seal. With direct contact between the heating element and the thermally conductive plate, sufficient heat energy is conducted to the thermally conductive plate to heat the entire plan area of the tissue in contact with the thermally conductive plate to sealing temperatures. Sealing temperatures, which are generally between 60° C. and 100° C., are achieved quickly because of the intimate contact between the heating element and the thermally conductive plate and the high thermal conductivity of the thermally conductive plate. Thermally isolating the thermally conductive plate from the forceps arms (a function provided by the sleeve) adds to the ability of the thermally conductive plate to quickly come up to temperature. The thermal resistance between the heating element and the thermally conductive plate results in temperatures that are always lower in the thermally conductive plate than in the heating element. This promotes tissue sealing in the thermally conductive plate area and tissue cutting in the heating element area. An added benefit of the thermally conductive plate is that it promotes even heating element temperatures due to increasing the effective longitudinal thermal conductivity of the heating element. Because the heating element and the thermally conductive plate are in intimate contact with very little thermal resistance between them the heating element longitudinal thermal conductivity is effectively improved because of the good longitudinal conductivity of the thermally conductive plate. This is very important when the heating element has uneven heat loads, as is usually the case. The high thermal conductivity of the thermally conductive plate allows it to transfer heat from one portion of the heating element to another colder portion of the heating element/thermally conductive plate assembly. This action pulls up the temperatures in the low spots and brings down the temperatures in the high spots. Bringing down the high temperatures is a benefit as very high temperatures, such as those in excess of 500° C., are undesirable. If temperatures below 300° C. are maintained, non-stick components such as PTFE or ePTFE (Teflon®) coatings will survive for the life of the device. Temperatures in excess of 300° C. will quickly destroy these components, and temperatures in excess of 600° C. may melt an aluminum heat spreader.

Current Starion® device heating element plan areas are 0.022" wide by 0.75" long or 0.010" wide by 0.750" long. Using the thermally conductive plate with these existing heating elements, at power level of about 10 watts, results in heated plan areas which can be increased by 5 times or more over the prior device. Heat spreader dimensions of 0.065 to 0.100" wide have proven effective in testing.

Dimensions of the various components and the appropriate power levels for the thermal cautery devices incorporating the heating element and heat spreader have been developed through testing on natural live tissue which closely approximates the sealing behavior of vascularized human body tissue. Specifically, live earthworms have been used in testing to develop the heat spreader design, thus making it quite convenient and inexpensive to test prototypes as necessary to optimize the geometry and material characteristics of the various components. As illustrated in FIG. 9, live red worms 53 of 2 to 5 mm diameter (approximating the thickness of tissues of interest such as veins and arteries) were sealed and divided, at positions between the clitellum 54 and the mouth 55. Prior to testing with the new devices, a number of earthworms in various conditions were tested with Starion® cautery forceps with well known effect on human and animal body tissue (having been tested with more expensive and burdensome animal testing and having been used commercially for some time) to determine there suitability. The earth worms proved to accurately model the response of live human tissue. To test the effectiveness of the thermal cautery devices, and to devise optimum component sizes and materials, live earth worms were sealed and divided with thermal cautery devices of various design. Earth worms of about 2 to 5 mm in diameter were used to model human vessels of 2 to 5 mm in diameter. The effectiveness of the thermal cautery devices was judged by the lateral extent of the sealed tissue, the width of the division (vaporized tissue at the line of division, and seal strength. The strength of the seal was judged by dividing a worm at two location to form a worm segment with seals at both ends, and then pressurizing the worm segment to ascertain that certain predetermined internal pressure would overcome the seal. Successful sealing and division of the earth worm models translated directly into successful sealing and division of animal and human tissue. The use of the earth worm as a model for tissue in the testing of cautery devices thus provides an inexpensive and convenient method of bench testing cautery devices. The method may be used with cautery devices comprising the resistive heating element and heat spreader disclosed above, RF cautery devices, and various other means for thermally affecting body tissue.

In use, the thermal cautery device is manipulated to grasp body tissue, such as a blood vessel, a small section of fat, or other tissue as necessitated by the desired surgery. With the grasping arms on either side of the target tissue, surgeons gently close the grasping arms or forceps, as the case may be, to bring the grasping faces into apposition, with the target tissue held between the faces. While applying pressure to the tissue with the grasping faces, the surgeon energizes the device to provide a DC current to the heating wire. The heating wire itself heats up to temperatures above about 200° C., thus vaporizing the tissue immediately between the heating wire and the opposing grasping face (and a small lateral extent of tissue). Heat is applied for a period of time, in the range of 5 seconds to 20 seconds, thus allowing heat from the heating element to conductively heat the heat spreader plate. Heat from the heat spreader plate, which typically reaches temperatures of 60° C. to 100° C., is thereby applied to the tissue trapped between the heat spreader plate and the opposing grasping face, resulting in a thermal seal of the tissue with a width closely corresponding to the plan area of the plate (less the small vaporized section).

The improvements to the thermal cautery device have been described in relation to laparoscopic ligation devices and forceps devices, but they may be applied to open surgical forceps and clamps, catheter-based devices, and various other embodiments of thermal cautery and thermal ligation devices. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of testing surgical devices comprising:
   providing a surgical device, said surgical device comprising means for thermally affecting body tissue of a human;
   providing an earth worm as a model of human body tissue;
   applying the surgical device to the earth worm and applying power to the device to thermally affect the earth worm;
   determining the suitability of the device for use on human body tissue based on the observed effect on the earth worm.

2. The method of claim 1 further comprising the steps of:
   providing the surgical device with first and second grasping arms adapted for closure about a section of human body tissue, said first and second grasping arms each having a grasping face, said grasping face on each grasping arm aligned to meet the grasping face of the other grasping arm upon closure of the grasping arms; wherein the means for thermally affecting body tissue comprises a means for applying energy to the human body tissue disposed between the grasping faces;
   grasping the earth worm between the first and second grasping faces;
   applying energy to the earth worm through the means for applying energy to thermally affect the earth worm.

3. The method of claim 2, wherein the step of providing a means for applying energy comprises providing a resistive heating element disposed proximate the grasping face of the first grasping arm so that it lies between the grasping face of the first grasping arm and the grasping face of the second grasping arm upon closure of the grasping arms, said resistive heating element being operably connected to a source of electrical power.

4. The method of claim 3, where in the step of providing means for applying energy further comprises providing a thermally conductive plate between the resistive heating element and one of the grasping arms.

5. The method of claim 1, 2, 3 or 4 further comprising the step of grasping the earth worm between the clitellum and mouth of the earth worm.

6. The method of claim 1, 2, 3 or 4 further comprising the step of modifying a component of the device based on the observed effect of the device on the earth worm.

* * * * *